US007722016B2

(12) United States Patent
Bradley et al.

(10) Patent No.: US 7,722,016 B2
(45) Date of Patent: May 25, 2010

(54) FLOAT FOR HUMIDIFICATION CHAMBER

(75) Inventors: Keith J. Bradley, Atlanta, GA (US);
Walter R. Sanders, Duluth, GA (US)

(73) Assignee: Medex Cardio-Pulmonary, Inc., Carlsbad, CA (US)

( * ) Notice: Subject to any disclaimer, the term of this patent is extended or adjusted under 35 U.S.C. 154(b) by 898 days.

(21) Appl. No.: 11/469,113

(22) Filed: Aug. 31, 2006

(65) Prior Publication Data
US 2008/0054500 A1  Mar. 6, 2008

(51) Int. Cl.
*B01F 3/04* (2006.01)
(52) U.S. Cl. .................. 261/70; 261/74; 261/DIG. 65
(58) Field of Classification Search .................. 261/62, 261/66, 68, 70, 72.1, 74, DIG. 65, 142
See application file for complete search history.

(56) References Cited

U.S. PATENT DOCUMENTS

| 4,051,205 | A | * | 9/1977 | Grant | 261/70 |
| 4,175,525 | A | * | 11/1979 | Johnson | 123/522 |
| 4,225,542 | A | | 9/1980 | Wall et al. | |
| 4,461,735 | A | | 7/1984 | Wirt | |
| 4,765,327 | A | * | 8/1988 | Shim | 128/204.13 |
| 5,195,515 | A | * | 3/1993 | Levine | 128/203.26 |
| 5,943,473 | A | | 8/1999 | Levine | |
| 6,988,497 | B2 | | 1/2006 | Levine | |
| 2004/0050386 | A1 | | 3/2004 | Levine | |

FOREIGN PATENT DOCUMENTS

EP 1733751 A1 12/2006
GB 1448473 9/1976

OTHER PUBLICATIONS

Medex product No. 1147 (3 pages, including Instructions for Use, Photographic image, and exploded drawing), 2007.
International Search Report for PCT/US2007/074094 mailed Dec. 14, 2007 (4 pages).
Written Opinion for PCT/US2007/074094 mailed Dec. 14, 2007 (6 pages).

* cited by examiner

*Primary Examiner*—Scott Bushey
(74) *Attorney, Agent, or Firm*—Wood, Herron & Evans, LLP

(57) ABSTRACT

A float for a humidification chamber has formed-in-place conformable seal, which may be accomplished by overmolding a thermoplastic elastomeric material to the float. The float may be comprised of sections sealingly joined together at an elevation above the water level defined by the buoyancy of the float and also above the water level within the humidifier chamber when filled.

13 Claims, 2 Drawing Sheets

FLOAT FOR HUMIDIFICATION CHAMBER

FIELD OF THE INVENTION

The present invention relates to humidification chambers, and more particularly, to a float for such chambers.

DESCRIPTION OF PRIOR ART

Humidification chambers provide a vehicle for imparting moisture and possibly heat to an air stream to assist with patient breathing. The chamber is adapted to hold water in its interior, such that a breathable gas passed over, or through, the water will pick up moisture as it passes through the chamber. Many such chambers are further adapted to be heated, such that the breathable gas is also warmed as may be desired for many situations. Importantly, it is desired to maintain a sufficient level of water in the chamber to facilitate the desired moisture and possibly heat transfer to the breathable gas.

The breathable gas may be coupled into the chamber interior via a gas inlet communicating through a wall of the chamber. The breathable gas passes over and/or through the water in the chamber, and back out to a patient via a gas outlet communicating through a wall of the chamber. A reservoir of water may be coupled to a water inlet of the chamber via a fluid line so as to maintain water in the chamber. In many cases, the water inlet is coupled through a top wall of the chamber and the water is fed into the chamber via a gravity feed through the water inlet.

In order to prevent the chamber from flooding, and to otherwise regulate the water level in the chamber, a float valve is provided within the chamber and through which water passes from the water inlet of the chamber. As is conventional, the float valve includes a generally buoyant float comprised of two sections, a top section and a bottom section, which are joined together along a weld line or seam. Typically, one or both of the sections is hollow so as to be buoyant and able to rise and fall with the water level in the chamber. The float top section includes an upper end confronting the water inlet, and the float bottom section has a lower end confronting a bottom wall of the chamber.

A separate, conformable seal, such as a silicone or rubber disk or pad, is inserted into a counter-bore in the upper end of the float. The seal may be mechanically held therein by insertion of a snap-ring or the like over the seal in the counter-bore. As the float rises, the conformable seal at the upper end impacts against a valve seat associated with the water inlet to close off communication between the chamber interior and the water inlet so as to shut off the flow of water when the level of water in the chamber is at or near its desired level. As the water level falls, the float falls causing its upper end to move away from the valve seat, thereby reestablishing communication between the chamber interior and the water inlet port so as to allow water to flow into the chamber if the water level falls below the desired level.

An example of a humidification chamber with a float valve is shown in Levine U.S. Pat. No. 5,943,473, owned by the assignee hereof and the disclosure of which is incorporated herein by reference in its entirety. In some situations, it may be desired to vent the chamber interior into the reservoir, as shown in Levine U.S. Pat. No. 6,988,497, also owned by the assignee hereof, and the disclosure of which is also incorporated herein by reference in its entirety. Products according to those patents are available from the assignee hereof or an affiliate, an example of which is product number 1147. While it is believed that chambers according to those patents do or will work well in their intended environment, improvements to the float are desired.

SUMMARY OF THE INVENTION

The present invention provides an improved float for a humidification chamber. It has been discovered that in some situations, the conformable seal might shift or become detached. To that end, and in accordance with the principles of one aspect of the present invention, a conformable seal is formed in place in the float upper end, such as by overmolding a thermoplastic elastomer thereto. Overmolding can be accomplished with conventional molding techniques, such as insert molding or multi-shot molding, by way of example. Overmolding creates a mechanical and/or chemical interlock of the seal and float upper end materials such that the seal is, effectively, integral with the upper end of the float and does not adversely shift or come away from the float.

A float may be formed in accordance with the foregoing aspect of the present invention by molding at least a portion of a rigid thermoplastic float housing including the float upper end, and then overmolding a conformable material, such as a low durometer thermoplastic elastomer, into the upper end to define a seal thereat. Advantageously, the portion of the float housing is the top section, and is advantageously hollow. The top section may be joined to a second float housing portion such as a bottom section thereof, the latter including the float lower end. The second housing portion may also advantageously be hollow.

Additionally, in some floats, the weld or seam joining the top and bottom sections of the float together ends up too close to, or even under, the water line. In some situations, exposing the seam to the water in the chamber can lead to leakage which may interfere with desired operation of the float and could lead to overfilling of the chamber. To that end, and in accordance with the principles of another aspect of the present invention, the float sections are sized such that the seam will be located well above the water level in the chamber when the float seal closes off the valve seat, and also above the water level defined by the buoyancy of the float. In particular, the buoyant float will generally extend partway into the water, but not so far as to bring the seam to the level of the water therearound.

By virtue of the foregoing, there is thus provided an improved float for a humidification chamber. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate an embodiment of the invention, and together with the general description of the invention given above, and the detailed description of the embodiments given below, serve to explain the principles of the present invention.

DETAILED DESCRIPTION OF THE DRAWINGS

Figure 1:
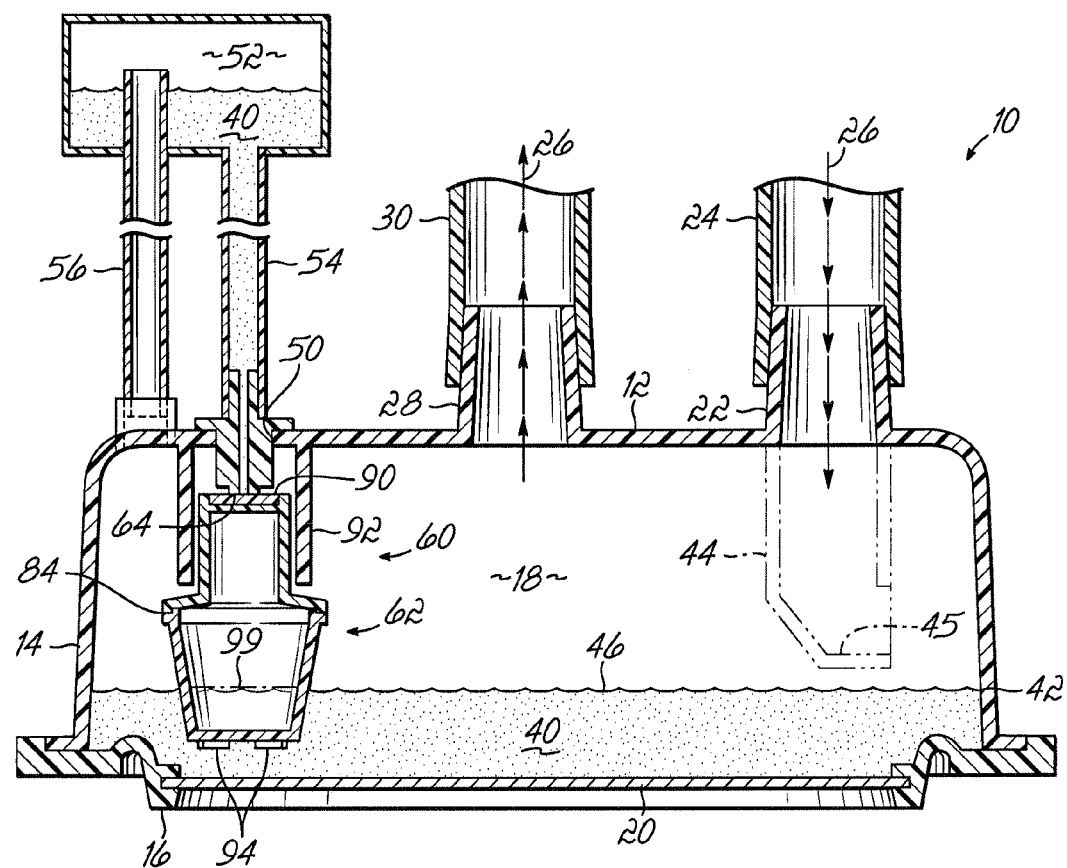
FIG. 1 is a cross-sectional, diagrammatic view of a humidifier chamber containing a float incorporating the various aspects of the present invention.

With reference to FIG. 1, there is shown an exemplary humidification chamber 10 having a top wall 12, a side wall 14, and a bottom wall 16 all joined together to define an interior 18 thereof. Walls 12 and 14 may be formed by a single plastic housing section. Bottom wall 16 is joined to side wall 14, and may include a heat conductive plate portion 20. Communicating through top wall 12 is a gas or air inlet 22, which may be coupled to an air hose 24 to receive breathable gas 26 into the interior 18 of chamber 10. Breathable gas passes out of chamber 10 via gas or air outlet 28, also communicating through top wall 12. Gas outlet 28 may be coupled via an air hose 30 to a patient (not shown) to provide breathable gas that has picked up moisture and possibly heat as it traveled through chamber interior 18 as is conventional.

Chamber 10 is adapted to hold water 40 in interior 18 thereof, usually up to a desired water level as at 42. Gas inlet 22 may advantageously include a tubular extension 44 (shown in dashed line) extending down into interior 18 towards the surface 46 of water 40 (or possibly into water 40). Tube 44 may include a deflector section 45.

As breathable gas 26 passes through interior 18, it will pick up moisture from water 40. Also, the water level will drop below the desired level 42. To maintain the desired level, water 40 may be replenished into chamber interior 18 via water inlet 50. Inlet 50 advantageously communicates through top wall 12 of chamber 10, so as to facilitate a gravity feed of water 40 from a reservoir 52 (such as a bag or bottle) coupled to water inlet 50 via fluid line 54. Reservoir 52 may optionally be vented into chamber interior 18 by a further line 56 which advantageously communicates into reservoir 52 above the water level therein, and may also include a check valve (not shown) in series therewith.

Figure 2:
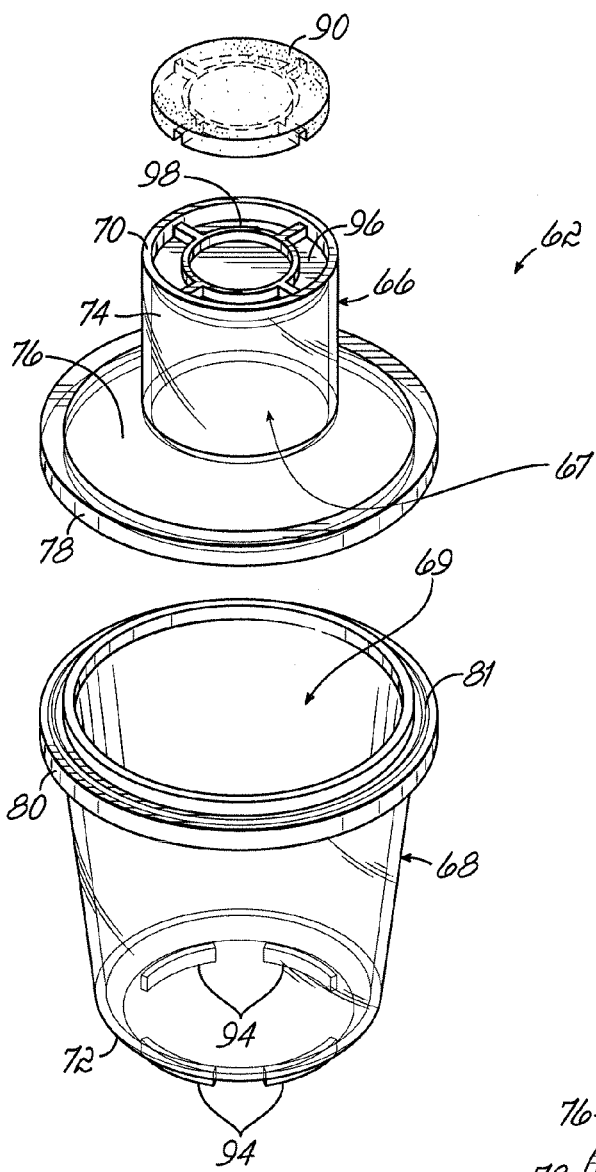
FIG. 2 is an exploded view of the float of FIG. 1.
Figure 3:
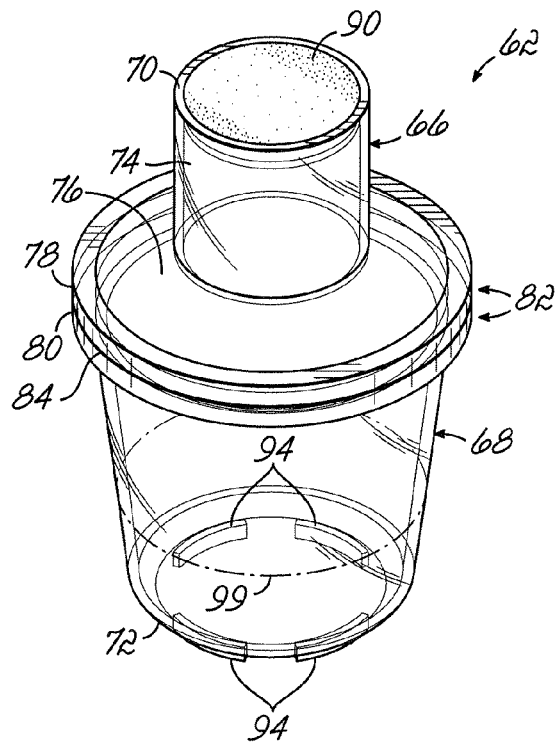
FIG. 3 is a perspective view of the float of FIG. 1.

To prevent chamber 10 from flooding, and to otherwise regulate the water level in chamber interior 18, a float valve 60 is provided within the chamber 10 and through which water 40 passes from the water inlet 50. Valve 60 includes a float 62 (FIGS. 2 and 3) and a valve seat 64 which cooperate to selectively open and close water inlet 50 thereby controlling communication of water into interior 18. In the embodiment shown herein, and with reference to FIGS. 2 and 3, float 62 has a top section 66 and a bottom section 68, each of which advantageously has a hollow interior 67, 69, respectively. Section 66 has an upper end 70 defining the upper end of float 62, and section 68 has a lower end 72 defining the lower end of float 62. Section 66 has an upper tubular portion 74, and a lower flanged portion 76 supporting a lower rim 78. Bottom section 68 is cup-shaped and has an upper rim 80 sized to mate with lower rim 78 of top section 66. Rims 78 and 80 are joined together, such as with plastic welding technologies like ultrasonic or spin welding, to define a buoyant float housing 82 with a generally sealed seam 84. Rims 78 and 80 may be shaped so as to interfit, and may include one or more energy directors, such as ridge 81 on rim 80, to facilitate the welding process as will be readily understood by those familiar with plastics welding. Top and bottom sections 66, 68 could, alternatively or additionally, be joined together in other ways, such as by solvent bonding, for example.

In accordance with one aspect of the present invention, a conformable seal 90 is formed in place in, or is integral to, upper end 70. With sections 66 and 68 joined together, float housing 82 is buoyant and so can rise and fall with the level of water 40 in interior 18. Extending from water inlet 50 is a tubular member 92 which includes therein valve seat 64. Tubular section 74 of top section 66 is dimensioned to fit slidingly within tubular member 92, such that upper end 70 confronts water inlet 50, and particularly valve seat 64 through which water inlet 50 communicates into interior 18 of chamber 10, and can move into contact with and away from valve seat 64. Float 62 rises with the water level until seal 90 impacts to conform against valve seat 64 to close valve 60, thereby closing off communication between the chamber interior 18 and the water inlet 50. The float 62 is dimensioned such that this occurs with the water 40 at about level 42, as seen in FIG. 1.

As water is consumed in the use of chamber 10, the level thereof will fall. So, too, will float 62 begin to fall, such that seal 90 will come away from valve seat 64, to once again open valve 60 and allow water 40 to flow into chamber 10, until float 62 rises to once again close valve 60. As the water level drops, lower end 72 of float 62 moves towards coming into contact with bottom wall 16, and especially portion 20, of chamber 10. To avoid the tendency of sticking thereat, lower end 72 is providing with one or more stand-off ribs 94 integrally formed in the molding of lower section 68. Should stand-off rib(s) 94 hit bottom wall 16 a water pathway will be maintained between bottom wall 16 and lower end 72 so as to reduce the tendency to stick thereat.

Advantageously, float 62 is formed by molding rigid thermoplastic to form at least a first portion of the float housing 82 and having upper end 70 with a counter-bore 96 and walls 98. A conformable material, such as a thermoplastic elastomer ("TPE"), is overmolded into the counter-bore 96 and around walls 98 of upper end 70 to define formed-in-place conformable seal 90 thereat which, due to the mechanical and/or chemical interlocking that occurs when TPE is molded to a rigid thermoplastic material, can result in seal 90 and upper end 70 being an integral piece.

The first portion, which may be top section 66, is advantageously molded to have a hollow interior 67. A second portion of float housing 82, such as bottom section 68, is advantageously molded of a rigid thermoplastic to have lower end 72 and stand-off rib(s) 94. That second portion, such as bottom section 68, is also advantageously molded to have a hollow interior 69. The two portions are sealingly joined as at seam 84 to define the float housing 82 with the upper and lower ends 70, 72 being oppositely disposed.

As seen in FIG. 1, the buoyancy of float 62 is such that a portion of float bottom section 68 will extend into the water to define a water level 99 of float 62 spaced above lower end 72. Top and bottom sections 66, 68 are sized such that their rims 78 and 80, respectively, join at seam 84 at an elevation spaced above lower end 72 by a distance greater than water level 99 defined by the buoyancy of float 62, and also above water level 42 with float valve 60 closed, to thus reduce the risk of leakage and/or overfilling of chamber 10. The spacing of rim 80, and hence seal 84, from lower end 72 may advantageously be at least about twice, and further advantageously at least about three times, the spacing of water level 99 from lower end 72.

Float 62 is advantageously of a dual durometer construction. To that end, sections 66 and 68 are molded of high durometer, rigid thermoplastic material, examples of which include high density polyethylene (HDPE), polypropylene (PP), polystyrene (PS), styrene-acrylonitrile (SAN), polycarbonate (PC), polyvinyl chloride (PVC), polymethyl methacrylate (PMMA), and polypropylene homopolymer such as Huntsman P4G4T-017. Seal 90 is advantageously overmolded of a softer, i.e., lower, durometer material so as to be conformable to valve seat 64. The material of seal 90 may be a TPE material, examples of which include thermoplastic polyurethane (TPU), thermoplastic copolyester (COP), thermoplastic polyolefin-elastomer blends (TPO), thermoplastic polyamides (PEBA), elastomeric alloys such as thermoplastics and cross-linked rubber (EA), and styrenic block copolymer such as GLS Dynaflex G2711. Seal 90 could be other than TPE material, examples of which include polydimethyl siloxane (PDMS), ethylene vinyl acetate (EVA), and [plasticized] polyvinyl choloride (PVC).

In use, water 40 selectively fills chamber interior 18 such as from a reservoir 52 through float valve mechanism 60. Water flow is shut off when formed-in-place seal 90 of float 62 impacts to conform to valve seat 64, and flows again as water drops off within chamber 10 such that float 62 moves away from valve seat 64. With sections 66 and 68 dimensioned such that seam 84 is at an elevation above water level 99, also above level 42 when chamber 10 is filled to close valve 60, float 62 is not susceptible to adverse leakage. Also, with seal 90 being formed in place to upper end 70, seal 90 is not susceptible to adverse shifting or coming away from upper end 70.

By virtue of the foregoing, there is thus provided an improved float for a humidification chamber.

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. For example, while reference is made to the top and bottom sections 66, 68 being directly joined together, they could be joined together through intermediate structures, or may include multiple portions in their own rights. The invention in its broader aspects is, therefore, not limited to the specific details, representative apparatus and method, and illustrative examples shown and described. Accordingly, departures may be made from such details without departing from the spirit or scope of the general inventive concept.

Having described the invention, what is claimed is:

1. A humidification chamber defining an interior adapted to hold water therein, the chamber comprising:
   a gas inlet, a gas outlet, and a water inlet each communicating into the interior;
   a valve seat associated with the water inlet;
   a bottom wall spaced below the water inlet, the bottom wall including an exposed conductive plate portion; and
   a buoyant float having a lower end confronting the conductive plate portion and supporting a seal being movable into and out of contact with the valve seat whereby to seal off the water inlet when water in the chamber exceeds a first level and open the water inlet when water in the chamber is below the first level, the float including a stand-off rib positioned to prevent the lower end of the float from contacting the conductive plate portion.

2. The humidification chamber of claim 1, the seal being a formed-in-place seal.

3. The humidification chamber of claim 1, the float being hollow.

4. The humidification chamber of claim 2, the seal being a conformable seal.

5. The humidification chamber of claim 1, the seal being a conformable seal.

6. The humidification chamber of claim 1, the seal being thermoplastic elastomer.

7. The humidification chamber of claim 1, the float further including top and bottom sections sealingly joined together at a seam, the seam being spaced above a water level of the float defined by the buoyancy thereof.

8. The humidification chamber of claim 7, the seam being spaced above the first level with the seal moved into contact with the valve seat.

9. The humidification chamber of claim 7, the seam being spaced above the lower end of the float a first distance, the water level of the float defined by the buoyancy being spaced from the lower end a second distance, the first distance being at least about twice the second distance.

10. The humidification chamber of claim 9, the first distance being at least about three times the second distance.

11. The humidification chamber of claim 7, the seal being supported by the top section.

12. The humidification chamber of claim 11, the top section being rigid plastic and the seal being thermoplastic elastomer.

13. The humidification chamber of claim 7, the stand-off rib being associated with the bottom section.

* * * * *